Figure 1:
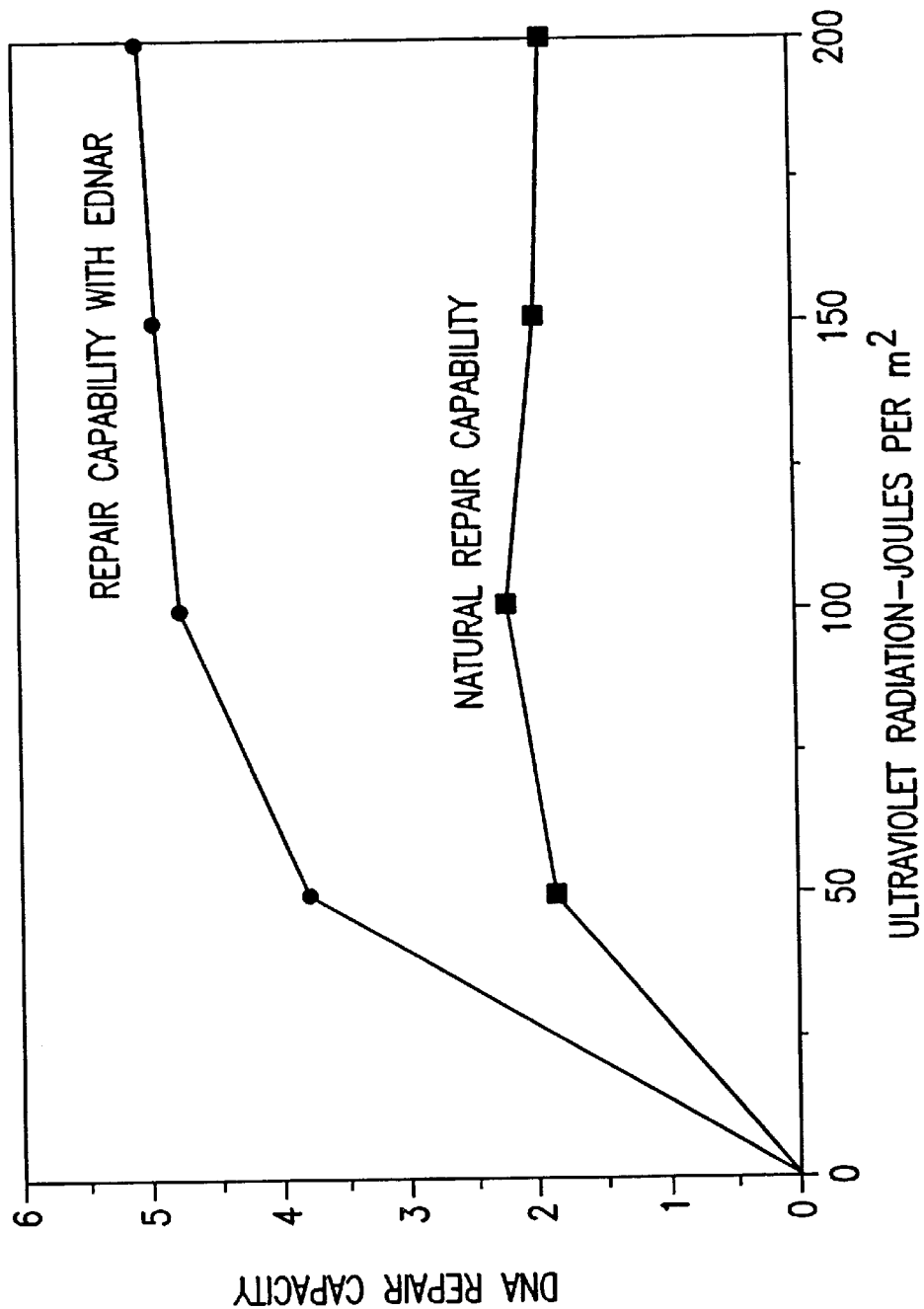

United States Patent

Riklis et al.

[11] Patent Number: 6,149,896
[45] Date of Patent: Nov. 21, 2000

[54] COSMETIC AND COSMECEUTICAL COMPOSITIONS

[76] Inventors: Emanuel Riklis, deceased, late of Beer-Sheva; by Ruth Riklis, legal representative, 10 Bar Kochba Street, 84231 Beer-Sheva; by Eran Riklis, legal representative, 10 Nelchet St., Tel Aviv 65215; by Liatt Oren-Riklis, legal representative, 14 Smats St., Tel Aviv; by Eitan Riklis, legal representative, 33 Dam Hamacabim St., Tel Aviv, all of Israel

[21] Appl. No.: 09/068,080
[22] PCT Filed: Oct. 30, 1996
[86] PCT No.: PCT/IL96/00135
    § 371 Date: Feb. 5, 1999
    § 102(e) Date: Feb. 5, 1999
[87] PCT Pub. No.: WO97/16155
    PCT Pub. Date: May 9, 1997

[30] Foreign Application Priority Data

Nov. 2, 1995 [IL] Israel ........................ 115851

[51] Int. Cl.[7] ............... A61K 7/42; A61K 7/40; A61K 7/00; A61K 31/05; A61K 31/455
[52] U.S. Cl. .............. 424/59; 424/400; 424/401; 514/354; 514/355; 514/356; 514/734; 514/844; 514/847; 514/886; 514/887
[58] Field of Search ................ 424/59, 60, 400, 424/401; 514/354, 355, 357, 734, 844, 847, 886, 887

[56] References Cited

U.S. PATENT DOCUMENTS 4,975,272  12/1990  Voyt .......................... 424/59
5,545,399  8/1996   Lee et al. .................... 424/59

Primary Examiner—Shelley A. Dodson
Attorney, Agent, or Firm—Evenson, McKeown, Edwards & Lenahan, P.L.L.C.

[57] ABSTRACT

Cosmetic and cosmeceutical compositions which enhance repair of damage caused to human DNA caused by excessive exposure to sunlight or to other radiation causing such damage. The active ingredients are a synergistic combination of nor-dihydroguiaretic acid (NDGA) and niacinamide. Optional components are propyl gallate or other antioxidants. Composition may further contain sun-screen additives.

8 Claims, 3 Drawing Sheets

COSMETIC AND COSMECEUTICAL COMPOSITIONS

BACKGROUND OF THE INVENTION

It is generally agreed that DNA damage and repair play a major role in the fate of living cells in terms of viability, mutagenesis and carcinogenesis, and aging. Skin cells are subject to continuous assaults by solar radiation, of which UVB is responsible for sunburns and skin cancer, while UVA is tanning. Both ranges of UV light are known to produce specific photoproducts, such as thymine dimers and the 6-4 photoproduct, and UVA has been shown to affect DNA strand breaks, in addition to formation of photoproducts, particularly as a result of attacks by reactive oxygen species.

The mechanism of excision repair, the major repair mechanism of damaged DNA, has been discovered in 1963 by Riklis (1964, 1965),(1),(2), Setlow and Carrier(3), (1964), and Boyce and Howard-Flanders (1964)(4). Since then, the generality of this repair pathway, as predicted by Riklis, was confirmed for many types of healthy cells and for different types of radiations, such as ultraviolet and ionizing radiations. Other modes of repair have been identified, including postreplication repair and strand break repair by ligation, and thus DNA damage and repair have become a most important event in cellular biology.

In 1981, Riklis(1)(2) had shown the possibility of enhancing DNA repair by the radioprotective compound WR-2721. He later showed the possibility of enhancing DNA repair by other chemical compounds, such as the vitamin nicotinamide.

The fact that ultraviolet assault on cells results in the formation of photoproducts is long known. In 1960 Beukers and Berends(5) identified thymine dimers (T<>T) as the product of irradiation of frozen thymine solutions with short UV radiation. In 1961 Wacker(6) identified T=T as the major photoproduct of UVC radiation which is responsible for cell death. It being the substrate of repair by photoreactivation was shown in 1962 by Rupert.

In 1963, as mentioned, thymine dimer was shown to be excised from DNA during the process of excision repair (Riklis(1)(2) Setlow & Carrier(3) Boyce & Howard-Flanders(4)). Other photoproducts have also been identified by various authors (Wang(7), Riklis(8) et al). A unique photoproduct was discovered by Riklis in DNA irradiated in a dry state, and a year later this product was found in spores and named the "spore product" (Setlow & Carrier(3)).

The excision repair pathways exist in normal healthy cells of mammals, plants and bacteria. Mutant bacteria exist which are deficient in repair, and in parallel there are human diseases which are manifested in extreme sensitivity to sun light (xeroderma pigmentosum) or to ionizing radiation (ataxia telangiectasia) and are deficient in cell ability to repair DNA.

FIELD OF INVENTION

The invention relates to cosmetic suncare compositions comprising in combination nor-dihydroguiaretic acid (NDGA), a known antioxidant with anti-inflammatory properties and niacinamide, optionally with BHT and propyl gallate. These include compositions in the form of post-exposure soothing creams, milks and ointments for soothing sunburns, which deep inside the skin cells enhance the repair of DNA from damages incurred during exposure to the sun. In addition, sunscreen preparations containing this combination of repair enhancers and antioxidants, reduce the degree of sunburn while acting towards enhancing repair from the instant damage. The small molecular weight of the compounds comprising EDNAR, "Enhanced DNA Repair", ensures penetration into skin cells and activity at the damage-sites in DNA.

The achievement of enhancing DNA repair by compounds which are of natural origin, NDGA and niacinamide, in an antioxidant environment is a breakthrough in suncare products which act not only as filters of UV radiation but provide further protection by an efficient repair of damages. These compounds, in cosmetic preparations, greatly improve the efficacy of such preparations by providing extra protection against UV light.

The discovery of DNA excision repair, showing that gaps may be formed in DNA and are filled by enzymatic means during the process of repair, has actually opened the way to the field of genetic engineering. Manipulation of genes, cutting sections of DNA out and introducing new sections in is a direct result of the observations of excision repair.

The main features of the invention are the combination of NDGA of the formula

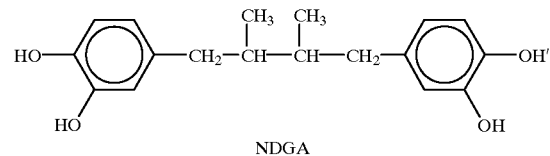

NDGA with niacinamide, which surprisingly result in substantial DNA repair due to the various UV radiations. The combination of these two compounds results in a synergistic effect.

It is advantageous to incorporate in the compositions of the invention a further antioxidant, such as propyl gallate. There are of course used conventional constituents, adjuvants and auxiliaries as generally used in cosmetic preparations.

Methods for Measuring DNA Repair Synthesis

Several methods exist for measurement of repair capacity of biological cells. The introduction of labelled thymidine into repair sites allows such measurements, but semiconservative DNA synthesis must be first inhibited in order to be able to measure repair synthesis. One commonly used method of inhibiting synthesis is with hydroxyurea, but we have developed a more efficient method in which semiconservative synthesis is stopped by trimethylpsoralen+UVA light (Riklis 1980(10), Heimer et al 1983(11), Riklis 1983 (10)). This method does not interfere with DNA repair synthesis and permits easy measurement of the repair capacity, as has been shown in many cultured fibroblast cell lines, as well as in endothelial cells (Vlodavsky et al, unpublished).

RESULTS

With the PUVA method, the repair capacity of various cell lines has been measured. In 1981 Riklis succeeded in enhancing the repair synthesis of DNA in cell cultures, following exposures to gamma radiation, accelerated electrons, neutrons, and UV light, by the addition of the well known radioprotector WR-2721 (aminopropyl aminoethyl phosphothioate) Riklis 1983(12). For this reason this protector is favoured for cancer radiotherapy as well as for military use. The significance of the advantage of WR-2721 over other classical radioprotectors such as cysteamine was enhanced when it was demonstrated that WR-2721 enhanced the repair capacity of DNA in irradiated cells, when added after the exposure to radiation, a phenomenon that does not occur with cysteamine. Another important study showed the effectivity of different radioprotectors on the formation and rejoining of DNA strand breaks. Ionizing radiations are known to cause more strand breaks than specific radiation products in DNA, particularly the more energetic particle radiations (alpha radiation, neutrons etc.). It has recently been shown that UVA radiation, the long ultraviolet rays, also bring about DNA strand breaks, probably through excited oxygen free-radicals such as $O^{2-}$ and the excited state singlet oxygen and oxidative products.

Measuring the effect of protectors on strand break formation showed strong effectivity of cysteamine and less of WR-2721, and still less of the vitamin niacinamide. However, when adding the protectors after the exposure to radiation, niacinamide was the most effective in enhancing the rejoining of DNA strand breaks, followed by WR-2721.

The next step in this research was to look for radioprotective and photoprotective effects of compounds which are not toxic, and the first example of success in this venture was with the use of the vitamin niacinamide Riklis et al (1990) (14). As already described, niacinamide is very effective in enhancing the rejoining of DNA strand breaks. Prior to that it has been shown that niacinamide is also effective in enhancing DNA repair synthesis, indicating enhanced excision repair. It should be stressed however that this enhancement is restricted to a low concentration of NA, up to three millimolar, as above that concentration it causes inhibition of repair. Niacinamide is an important protector from ionizing radiations, or from UVA radiation which causes breaks similar to those caused by ionizing radiation. A better enhancer of repair from short wave UV light was required and was found in the form of the antioxidant NDGA (nor-dihydro guiaretic acid).

NDGA was shown to enhance the repair synthesis following both ultraviolet and ionizing radiations. Furthermore, it enhances the repair of damages formed in DNA by trimethylpsoralen+UVA light (365 nm).

The following Graphs 1, 2 and 3, in the Table show clearly the extent of enhancement of DNA repair capacity by the compounds nicotinamide and NDGA.

LEGEND TO FIGURES

FIG. 1: DNA Repair Capacity of human fibroblast cells exposed to UVC radiation. Repair capacity is the ratio of the number of counts per minute of tritiated thymidine at each dose, divided by the number of counts at zero dose.

DNA repair capacity without addition of modifier;

DNA repair capacity in the presence of 3mM nicotinamide plus 2mM NDGA (the EDNAR combination). This give average of many experiments.

Figure 2:
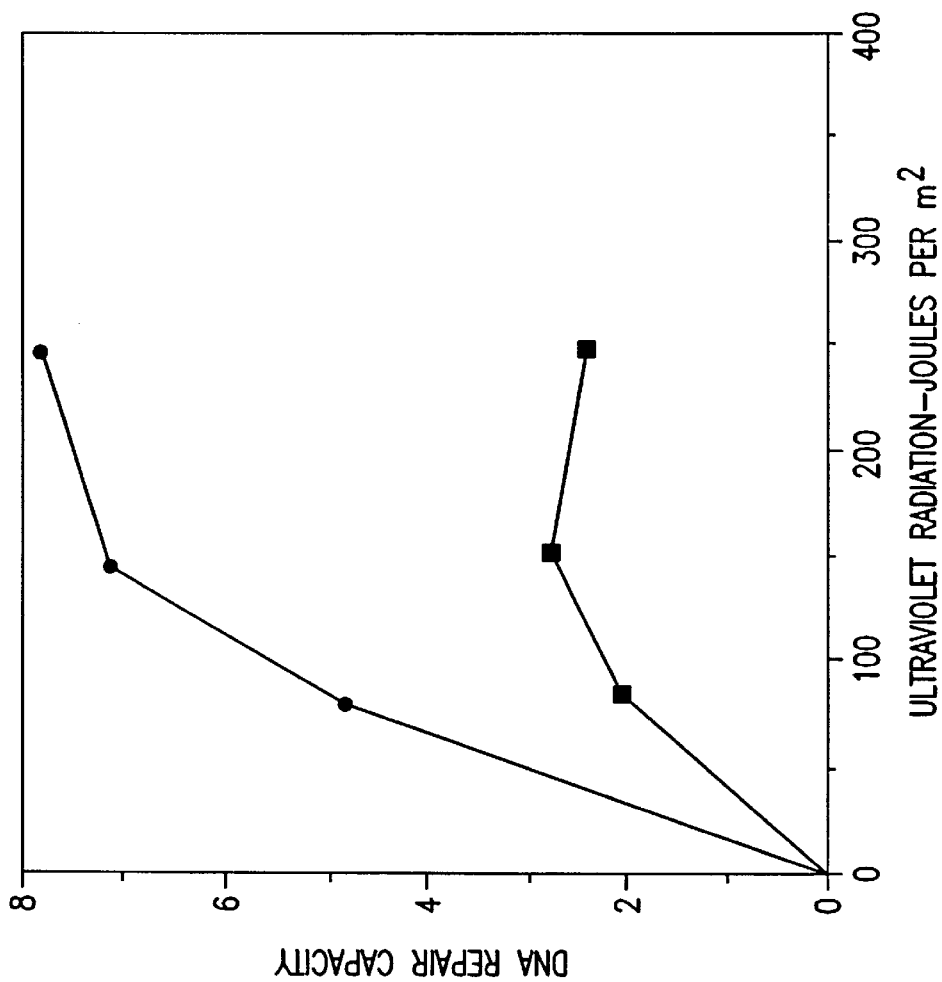

FIG. 2: Another single experiment identical to that in FIG. 1.

Figure 3:
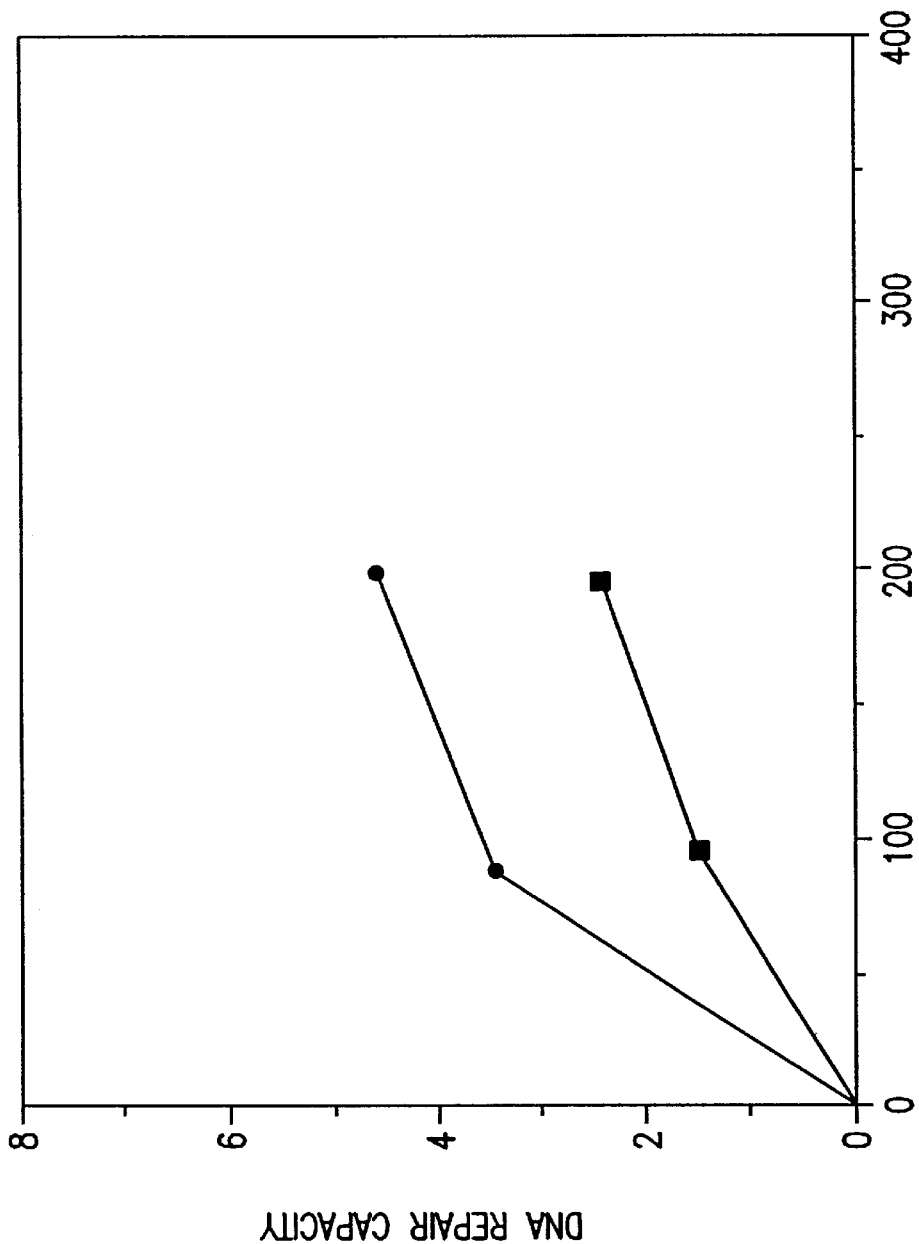

FIG. 3: DNA repair capacity of human fibroblast cells exposed to X-irradiation. All other conditions and symbols are the same as in FIG. 1 single experiment.

COSMETIC PREPARATIONS

In cosmetic preparations, in addition to the usual components, such as oils, esters, alcohols etc., specific compounds have been incorporated in order to obtain an antioxidative environment, together with compounds which enhance DNA repair. Thus, BHT and Propylgallate are added as antioxidants, NDGA is added both as an antioxidant and a repair enhancer, and nicotinamide serves as repair enhancer. All of these compounds are recognised by the CTFA as cosmecetics, and some even as food additives, fit and approved for human consumption.

The concentrations used are in the following ranges:

Niacinamide: up to 3 mM.

NDGA: between 0.001% to 0.01%. BHT: 0.005 to 0.02%:
Propylgallate: 0.002 to 0.02%.

In addition to these EDNAR compounds, the preparations may include various common cosmetic reagents, such as:

A. In After-Sun lotions and Creams: Deionized water, wheatgerm oil, Vitamin A and E, isopropyl palmitate, carbomer, emulsifying vegetable wax, ethyl alcohol, jojoba oil, aloe vera gel, lavender oil, isopropyl myristate, lecithin, tocopherol (vit. E.), lactic acid, tartaric acid, glycolic acid, salicylic acid, ascorbic acid, gluconic acid, citric acid, (fruit acids), phenonip, vitamin BI, Vitamin C, DMDM, Hydantoin and iodopropynil butylcarbamate, Dead Sea minerals, vanilla extract and other fragrances, Dead Sea water.

B. After-Sun Gel: Water, aloe vera gel, ethyl alcohol, carbomer, phenonip, glydant plus, peppermint oil, perfume, and the EDNAR compounds: niacinamide (vitamin pp or B3), antioxidants BHT, and NDGA, and propylpallate.

C. Sunscreen lotions and creams with a determined SPF number will contain, in addition to the EDNAR compounds, active ingredients such as Titanium dioxide, ZnO, Octyl Methoxy Cjunamate and Parsol 1789, and Benzophenone #3 and Octocrylene MCX in different concentrations to achieve the desired SPF (sun protection factor) number.

The common cosmetic ingredients in these preparations may include different combinations of the following:

Mineral oil, glyceryl stearate, stearic acid, glycerin, silicone 1401, propylene glycol, phenonip, glydant plus, D-alphatocopherol acetate, isopropylmyristate, cetyl stearyl alcohol, carbopol, triethanolamine, cyclomethicone & dimethicone, ppf-10 methylglucose ether, polyquaternum-37, dicaprilate dicaprate, citric acid, ppg-1 tricedeth-6, Dead Sea minerals, perfume.

The combination of niacinamide and NDGA ensures the enhancement of DNA repair from damages caused by both UVA and UVB, as well as from effects of UVC (from artificial sources) and from ionizing radiation.

These features in the novel cosmetic preparations afford improved protection to persons in the following situations: persons exposed to sunlight during work or leisure, including workers in agriculture, building, drivers, soldiers during training, seamen.

The novel cosmetic preparations offer improved protection to persons in the following situations: persons exposed to sunlight during their work or leisure, including workers in agriculture, building, drivers, soldiers during training, seamen, employees in hospitals and industry, who are in the vicinity of radioactive isotopes or radiation sources, namely in departments of radiotherapy, radiology, nuclear medicine etc., actually it is beneficial to the population at large. In view of recent research results concerning the emission of UV radiation from halogen lamps and even from ordinary fluorescent lamps, resulting in reported increased incidence of melanoma among office workers, such an all day repairing lotion is recommended to everyone for daily use.

There is a vast amount of literature on the beneficial properties of the compound NDGA, including its action as an antioxidant, antiinflammatory, etc. The property of acting as an enhancer of repair of DNA from both ionizing and ultraviolet radiations is a newly discovered feature.

These preparations offer for the first time improved protection from sunlight coupied with reducing DNA damage by enhancing its repair, processes which promise reduced risk of mutations and of development of skin cancer.

The following are examples of compositions which contain the essential components of the invention, and in addition various additives and adjuvants.

| SKIN REPAIR, AFTER SUN LOTION | |
|---|---|
| Deionized water | ad 100 ml |
| vegetable oil | 12.7% |
| isopropyl palmitate | 11.4% |
| emulsifying wax | 3% |
| isopropyl myristate and | 0.5% |
| lecithin and tocopherol | |
| citric acid | 1% |
| wheatgerm oil | 1% |
| phenonip | 0.4% |
| cetearyl alcohol | 0.5% |
| glydant plus | 0.2% |
| perfume | 0.2% |
| aloe vera gel | 0.1% |
| jojoba oil | 0.1% |
| niacinamide | 0.02% |
| BHT | 0.01% |
| propyl gallate | 0.005% |
| nordihydro guiaretic acid | 0.003% |
| SUNCREAM SPF 16 | |
| Deionized water | ad 100 ml |
| isopropyl palmitate | 8% |
| polyguaternium 37 and | |
| mineral oil and | |
| ppg-1 trideceth-6 | 3% |
| benzophenone-3 | 3% |
| octylmethoxycinnamate | 5% |
| phenonip | 0.2% |
| niacinamide | 0.02% |
| BHT | 0.01% |
| propyl gallate | 0.005% |
| nordihydroguiaretic acid | 0.003% |

DNA REPAIR CAPACITY OF FIBROBLAST CELLS WITH "EDNAR" COMPOSITIONS

Measurement of incorporation of tritiated thymidine into DNA in which semiconservative synthesis has been inhibited by treatment with trimethylpsoralen+UVA light (PUVA). Thymidine incorporated is a measure of repair synthesis (also called UDS).

| REPRESENTATIVE EXPERIMENT | | | |
|---|---|---|---|
| Conditions | Counts per minute per plate | Difference | Ratio |
| untreated | 80,000 | | |
| PUVA treated | 200 | | |
| UV 80 J/m$^2$ | 425 | 225 | 2.125 |
| UV 80 J/m$^2$ + EDNAR | 880 | 780 | 4.90 |
| UV 150 J/m$^2$ | 750 | 550 | 2.75 |
| UV 150 J/m$^2$ + EDNAR | 1450 | 1250 | 7.25 |
| UV 250 J/m$^2$ | 700 | 500 | 2.50 |
| UV 250 J/m$^2$ + EDNAR | 1600 | 1400 | 8.00 |
| X-ray 100 Gy | 300 | 100 | 1.50 |
| X-ray 100 Gy + EDNAR | 850 | 350 | 3.25 |
| X-ray 200 Gy | 510 | 318 | 2.55 |
| X-ray 200 Gy + EDNAR | 800 | 700 | 4.50 |

REFERENCES

1. Riklis E., Repair of ultraviolet irradiated deoxyribonucleic acid in vivo and in vitro. Annual Meeting Israel Soc. Microbiol., Jerusalem, May 1964; Israel J. Medical Sciences 321, 1965.
2. Riklis E., Studies on mechanism of repair of UV-irradiated viral and bacterial DNA in vivo and in vitro. Canadian J. Biochem. 43, 1207–1219, 1965.
3. Setlow R. B. and Carrier W. L. The disappearance of thymine dimers from DNA: an error-correcting mechanism. Proc. Natl. Acad. Sci. USA 51, 226–231, 1964.
4. Boyce R. P. and Howard-Flanders P., Release of ultra-violte light-induced thymine dimers from DNA in E.coli K-12. Proc. Natl. Acad. Sci. USA 51, 293–200, 1964.
5. Beukers R. and Berends W., Biochim. Biophys. Acta 41, 550. 1960.
6. Wacker A., Delweg H. and Weinblum D., Naturwiss. 47, 477, 1961.
7. Wang S. Y., J. Am. Chem. Soc. 93, 2554, 1971.
8. Riklis E., Photoproducts and their significance in radiation damage repair in "Novas Tendencies em Fotobiologia", Symp. Int.; Academia Brasileira de Ciencias 45, 221, 1973.
9. Donnelan J. E. and Setlow R. B., Science 149, 308, 1965.
10. Riklis E., Aspects of research on low level radiation and late effects in "DNA Repair and Late Effects" (Edit: H. Altmann, E. Riklis, H. Slor) 3–13, 1980, NRCN Press.
11. Heimer Y. M., Kol H., Shilow Y. and Riklis E., Psoralen plus near ultraviolet light: a possible new method for measuring DNA repair syntheses. Radiat. Res. 95(3), 541–549,1983.
12. Riklis E., DNA repair as a probe of radiosensitivity and radioprotection in "Radioprotectors and Anticarcinogens" (Edit: O. F. Nygaard and M. G. Simic) 363–380,1983, Academic Press.
13. Riklis E., Kol R., Green M., Prager A., Marko M., Mintsberg M., Increased radioprotection attained by DNA repair enhancement. Pharmacol and Therapeutics 39, 311–322, 1988.
14. Riklis E., Kol R. and Marko R., Anticarcinogenicity and improved radioprotection by enhancement of DNA repair: the role of nicotinamide in "Frontiers in Radiation Biology" (Edit: E. Riklis) 175–190, 1990, VCH Weinheim.

What is claimed is:

1. A cosmetic and cosmeceutical composition for DNA repair of damages caused by excessive sun exposure or exposure to any other radiation causing DNA disruption, or modification which comprises in combination an effective quantity of nor-dihydroguiaretic acid (NDGA) of the formula

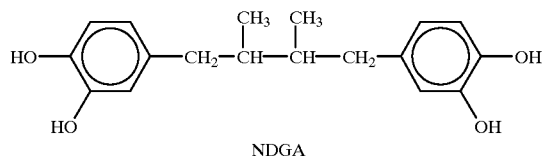

NDGA and niacinamide, with conventional carriers, adjuvants or auxiliaries.

2. A composition according to claim 1 which additionally contains propyl gallate.

3. A composition according to claim 1, containing a further antioxidant.

4. A composition according to claim 1, in the form of a sun-screen preparation containing in addition a compound selected from titanium dioxide, Parsol MCX, Parson 1789, Eusolex(T.M.) bezophnone #3, cetyl methoxy cinnamate octocrylene.

5. An enhanced DNA composition according to any of claims 1, in the form of after-sun lotions or creams, after-sun gels, sunscreen lotions and creams, radiation protection creams or gels, after radiation DNA repair compositions.

6. A composition according to claim 2, in the form of a sun-screen preparation containing in addition a compound selected from titanium dioxide, Parsol MCX, Parson 1789, Eusolex(T.M.) bezophnone #3, cetyl methoxy cinnamate octocrylene.

7. An enhanced DNA composition according to claim 2, in the form of after-sun lotions or creams, after-sun gels, sunscreen lotions and creams, radiation protection creams or gels, after radiation DNA repair compositions.

8. An enhanced DNA composition according to claim 3, in the form of after-sun lotions or creams, after-sun gels, sunscreen lotions and creams, radiation protection creams or gels, after radiation DNA repair compositions.

* * * * *